United States Patent [19]

Shive

[11] Patent Number: 4,499,064
[45] Date of Patent: Feb. 12, 1985

[54] ASSESSMENT OF NUTRITIONAL STATUS OF INDIVIDUALS

[75] Inventor: William Shive, Austin, Tex.

[73] Assignee: Clayton Foundation for Research, Houston, Tex.

[21] Appl. No.: 492,308

[22] Filed: May 6, 1983

Related U.S. Application Data

[63] Continuation-in-part of Ser. No. 384,822, Jun. 3, 1982, abandoned.

[51] Int. Cl.³ .................... G01N 1/00; G01N 33/48; C12Q 1/00; C12N 5/00
[52] U.S. Cl. .......................................... 424/2; 435/4; 435/29; 435/240; 435/241
[58] Field of Search ............... 424/2; 435/4, 29, 240, 435/241; 23/230 B

[56] References Cited

U.S. PATENT DOCUMENTS

Re. 309,985  6/1982  Cartaya ........................ 435/241
4,282,326  8/1981  Moldenhauer ................ 435/240
4,302,437  11/1981  Herbert ........................ 424/2

OTHER PUBLICATIONS

Chem. Abst. 94, 2287(p), (1981)–Goodwin et al.

Primary Examiner—Douglas W. Robinson
Attorney, Agent, or Firm—Fulbright & Jaworski

[57] ABSTRACT

Disclosed is a culture medium and methods for lymphocyte assessment of the nutritional status of humans by which repeatable and quantitative assays for deficiencies, abnormal requirements for or imbalances of vitamins, minerals and amino acids; for carbohydrate utilization, metabolism and imbalances and the like are obtained so that nutrition for each individual can be optimized thereby providing a significant impact on human health and productivity. Minimal amounts of lymphocytes and components of the culture medium are utilized making it possible to conduct a large number of nutritional assays with a small sample of blood.

20 Claims, No Drawings

4,499,064

ASSESSMENT OF NUTRITIONAL STATUS OF INDIVIDUALS

CROSS REFERENCE TO RELATED APPLICATION

The present invention is a continuation-in-part of application Ser. No. 384,822 filed June 3, 1982, now abandoned in favor of this application.

FIELD OF THE INVENTION

The present invention is in the field of nutritional assessment and treatment of individuals so that the nutritional requirements of the individual can be optimized to provide improved health and productivity.

BACKGROUND OF THE INVENTION

The ability to alleviate clinically recognizable diseases, such as pellagra and pernicious anemia, by nutritional factors led to the discovery of several vitamins and to the association of definable disease states with specific nutrient deficiencies. Because these diseases are diagnosed clinically and can be confirmed by laboratory tests, nutritional treatment of these diseases was quickly incorporated into medical practice.

Although considerable evidence has accumulated for a broader link between nutrition and disease, behavior, performance and well-being of human-kind, the incorporation of such concepts into general medical practice has not been accomplished largely because methods for assessment of individual nutritional status are lacking. Data such as blood and urine levels of nutrients, degree of saturation of enzymes with coenzymes derived from specific vitamins, and analyses of hair have been compared with a range of normal values in attempts to determine nutrient deficiencies. However, such methods do not actually determine the nutritional requirements of an individual, and on the basis of biochemical individuality, nutritional requirements—particularly the quantitative needs—are known to vary significantly among different "normal" individuals. In short, these previous methods of assessment have merely determined the nutrient levels, nutrient intakes, etc. and compared these with the averages of control groups. These previously used methods did not allow for individual variations which affect everyone to a greater or lesser degree.

In the absence of suitable clinical tests for assessing individual status, attempts in medical practice to utilize nutritional therapy have been limited. A "well-balanced" diet sometimes with limited vitamin supplementation has been the most common approach in medical practice to nutrition of individual patients. More limited in medical practice has been the mega-vitamin approach, one which has received considerable criticism on the basis of limited experimental evidence for possible detrimental effects, lack of data concerning possible long term adverse effects, and lack of convincing evidence for a beneficial effect in the treatment of particular disease states.

For some time, it has been apparent that effective utilization of nutrition in medical practice is dependent upon the development of methods for assessing the nutritional status of each individual and identifying factors which limit the nutritional responses of each individual. It would be anticipated that optimizing nutrition for each individual would have a very significant impact on human health and productivity.

Several years ago I initiated an approach to this problem through an assessment of the nutritional variability of cell cultures derived from individuals participating in the study. After a number of potential types of cells had been considered, lymphocytes from blood were selected, primarily because of their availability on a routine basis from patients. Lymphocytes have the further advantage of being metabolically inactive until activated by a mitogen so that these cells carry information concerning past nutritional status and have little day to day variation in nutritional responses. In the activation and initiation of growth, the lymphocytes must carry out most of the reactions required of any of the growing cells of the body; consequently, it would be anticipated that abnormalities in the nutritional requirements or metabolism of lymphocytes would likely reflect the condition in other cells. Also, appropriate intervention by supplementation, or in the case of toxicities appropriate limitation of the toxic substance or reversal of its effect by dietary supplements, would be beneficial for the individual.

In order to develop such a method, it was necessary that lymphocytes be cultured in a chemically defined medium without the usual supplementation of fetal calf serum. Although activation of lymphocytes under serum-free conditions had been reported, difficulties reported in achieving the same results in different laboratories led to the suggestion that possibly trace serum contaminants or other artifacts were involved in the serum-free experiments. Serum albumin or unidentified serum macromolecules were reported to be absolutely essential for mitogen-induced DNA synthesis in human peripheral blood lymphocytes.

In initiating the present invention, a number of chemically defined media which had been used in cell culture were found to support only marginal activation and very limied growth of lymphocytes. It became apparent that new media would have to be developed in order to obtain significant growth responses. In order to obtain media suitable for assessment of the nutritional status of lymphocytes, it was necessary to develop a medium in which components were adjusted to minimal concentrations but at a level which would still not limit the optimal response of the lymphocytes. Each change required determination of the effect on the response of other components.

SUMMARY OF THE INVENTION

The present invention is directed to an assay and a culture medium used in the assay by which a very broad survey of the deficiencies or abnormal requirements of nutrients, sensitivity to nutrient imbalances, sensitivity to toxic effects of nutrients, drugs, and a wide variety of substances, and many biosynthetic capabilities for each individual can be determined. In short, the present invention for the first time makes it possible to determine accurately the nutritional status and requirements, the quantitative needs, of an individual so that effective utilization of nutrition by the individual can be determined and implemented. The term "nutrients" as used herein means those nutrients necessary for growth, normal functioning and maintaining life. These nutrients include vitamins, amino acids (proteins), minerals, carbohydrates, and lipids (fats).

In short, lymphocytes are cultured in a serum-free, buffered culture medium from which individual or groups of components can be omitted and/or to which various possible components of blood including abnormal components, such as drugs, can be added. The cultures are harvested and the responses of the lymphocytes are measured. For example, when testing for vitamine deficiencies or abnormalities in vitamin responses, the vitamin to be tested is omitted from the culture medium. One set to be used as a control contains all of the vitamins. In testing for sensitivity to amino acid imbalances, all of the thirteen amino acids which are essential for lymphocytes and serine and glycine which may be required by many individuals are present, and each or a group of amino acids at concentrations which are normally present in blood and at slightly higher concentrations are tested for inhibitory effects. In testing for carbohydrate utilization, glucose can be omitted from the medium and the responses to each of many other carbohydrates (such as mannose and galactose), can be determined.

The culture medium for determining the optimal nutritional requirements for lymphocytes comprises a serum-free, buffered solution of inorganic salts, glucose, amino acids, vitamins, pyruvate, choline, inositol and adenine. The pH is adjusted to 7.6. An antibiotic supplement is added to assist in suppression of contamination by other organisms, and calcium chloride and magnesium sulfate solutions, ferrous sulfate and ethylene-diamine tetraacetic acid (EDTA) are included. Deionized water is included to provide a final volume and the culture medium is filtered through filter units for sterilization. After filtration, a mitogen such as a sterile solution of phytohemogglutinin (PHA) is added to the culture medium.

A more detailed description of the culture medium and methods of the assay are set forth in the following description of presently-preferred embodiments of the invention.

Accordingly, it is an object of the present invention to provide a culture medium by which a broad survey of the deficiencies or abnormal requirements of nutrients, sensitivity to nutrient imbalances, sensitivity to toxic effects of nutrients, drugs, and a wide variety of substances, and many biosynthetic capabilities for each individual can be determined.

It is a further object of the present invention to provide a lymphocyte method of assessment of the nutritional status of individuals which provides repeatable and quantitative results.

It is a further object of the present invention to provide such an assay in which very small quantities of blood are sufficient for the lymphocyte assay.

A further object of the present invention is the provision of such an assay which is repeatable and quantitative for the determination of deficiencies, abnormal requirements for or imbalances of vitamins, minerals, essential amino acids, carbohydrates and other nutrients and biochemical intermediates and in which minimal quantities of culture components are used which interact to provide these repeatable quantitative results.

Other and further objects, features, and advantages appear throughout.

DESCRIPTION OF PRESENTLY PREFERRED EMBODIMENTS

As previously mentioned, the present invention is directed to a lymphocyte assay of the nutritional status of man by which the deficiencies or abnormal requirements of nutrients, sensitivity to nutrient imbalance, sensitivity to toxic effects of nutrients, drugs and a wide variety of substances, and many biosynthetic capabilities for each individual can be determined so that nutrition for each individual can be optimized to provide improved health and productivity of the human being. In order to accomplish this result, it is necessary to have a culture medium in which the components are adjusted to minimal concentrations but at a level which will still not limit the optimal response of the lymphycytes and in which the components of the culture medium do not have an adverse effect on the response of the lymphocytes.

In using the culture medium for certain types of tests, omissions are appropriately made from the complete medium of vitamins, amino acids, and inorganic salts, etc., and the effect of the nutrient omitted is determined. For example, the complete vitamin supplement is omitted from the culture medium when testing for vitamins and an aliquot of a vitamin solution from which the vitamin to be tested has been omitted is added individually to each tube. One set of triplicates, to be used as a control, contains all the vitamins. In testing for amino acid imbalances, however, all of the 15 amino acids are included and supplements of high concentrations of each naturally occurring amino acid, or a group of amino acids, to be tested are included.

A presently preferred culture medium for determining the optimal nutritional requirements for lymphocytes includes the following components and is prepared as follows:

SOLUTIONS

Double Strength Medium Buffer—The double strength medium buffer used contains per liter of deionized water: Hepes (buffer), 23.8 g.; sodium hydroxide, 1.28 g.; sodium chloride, 14.02 g.; dipotassium hydrogen phosphate, 1.05 g.; and phenol red, 2.48 mg. This buffer is filtered through a 0.22 $\mu$m. Millipore filter.

Medium Salts—The medium salts stock solution used for washing and suspending the lymphocytes is prepared by diluting the double strength medium buffer 1:2 with deionized water. Glucose when used as an optional component is added to a final concentration of 4 mM. The pH is then adjusted to 7.6 with 4N NaOH and the solution is filtered. Supplements are added to a measured amount of this stock solution giving a final concentration of 55.5 mg/l calcium chloride, 60.0 mg/l magnesium sulfate, 0.695 mg/l ferrous sulfate and 0.373 mg/l EDTA. The ferrous sulfate and EDTA are prepared and added together. The final solution is then refiltered. In tests for mineral requirements, the appropriate minerals are omitted from the medium salts.

Amino Acid Supplement—The amino acid supplement used contains per liter: 0.7 g. L-arginine, 5.85 g. L-glutamine, 0.25 g. glycine, 0.23 g. L-histidine, 0.13 g. L-isoleucine, 0.44 g. L-leucine, 1.22 g. L-lysine, 0.15 g. L-methionine, 0.0825 g. L-phenylalanine, 0.35 g. L-serine, 0.4 g. L-threonine, 0.034 g. L-tryptophan, 0.063 g. L-tyrosine, and 0.39 L-valine. If desired the glutamine can be added separately. Cysteine is added separately with pyruvate, as subsequently indicated.

Vitamin Supplement—The vitamin supplement used contains per liter: 0.735 mg. biotin, 0.602 mg. folinic acid (calcium salt), 0.61 g. nicotinamide, 23.8 mg. calcium pantothenate, 6.15 mg. pyridoxine, 33.7 mg. thiamin, 13.6 mg. vitamin $B_{12}$, and 3.75 mg. riboflavin.

Antibiotic Supplement—The antibiotic supplement used contains per liter: 10,000,000 IU penicillin, 10,000,000 μg. streptomycin and 25,000 μg. amphotericin B (Fungizone).

Phosphate Buffered Saline—The phosphate-buffered saline solution contains per liter: 7.1 g. NaCl, 2.17 g. Na$_2$HOP$_4$.7H$_2$O, 200 mg. KH$_2$PO$_4$; and 200 mg. KCl.

CULTURE MEDIUM

A presently-preferred culture medium suitable for determining the optimal nutritional requirements for lymphocytes is prepared as follows: To 50 ml. of medium buffer is added 72 mg. glucose, 1 ml. amino acid supplement, 3 ml. of a 5.5 mg/ml pyruvate—0.88 mg/ml cysteine solution, 1 ml. of a 1.4 mg/ml choline chloride—1.8 mg/ml inositol solution, 1 ml. of the above indicated vitamin supplement, and 1 ml. of a 135 μg/ml adenine solution. The pH is adjusted with dilute NaOH to 7.6. Supplements of the following are then added: 1 ml. of the antibiotic supplement, 0.5 ml. of a 22.2 mg/ml calcium chloride solution, 0.5 ml. of a 24 mg/ml magnesium sulfate solution, 1 ml. of a solution of 0.278 mg/ml ferrous sulfate in 0.149 mg/ml EDTA. Deionized water is added to a final volume of 100 ml. and the medium is filtered through Nalgene membrane filter units for sterilization. After filtration 0.2 ml. of a 1 mg/ml sterile solution of phytohemagglutinin (PHA) is added to each 100 ml. of media. PHA is obtained from Sigma Chemical Co. in 5 mg. quantities and is diluted with sterile, deionized water.

Accordingly, a presently-preferred culture medium suitable for determining the optimal nutritional requirements for lymphocytes comprises a serum-free, buffered (pH 7.6) solution in deionized water containing the following per liter of solution:

TABLE I

| Carbohydrate | |
|---|---|
| Glucose | 720 mg. |
| Amino Acids | |
| L-Arginine hydrochloride | 7 mg. |
| L-Cysteine hydrochloride hydrate | 26.4 mg. |
| L-Glutamine | 58.5 mg. |
| Glycine | 2.5 mg. |
| L-Histidine hydrochloride hydrate | 2.3 mg. |
| L-Isoleucine | 1.3 mg. |
| L-Leucine | 4.4 mg. |
| L-Lysine hydrochloride | 12.2 mg. |
| L-Methionine | 1.5 mg. |
| L-Phenylalanine | 0.825 mg. |
| L-Serine | 3.5 mg. |
| L-Threonine | 4.0 mg. |
| L-Tryptophan | 0.34 mg. |
| L-Tyrosine | 0.63 mg. |
| L-Valine | 3.9 mg. |
| Vitamins | |
| Biotin | 7.35 μg. |
| Folinic acid (calcium salt) | 6.02 μg. |
| Nicotinamide | 6.1 mg. |
| Pantothenic acid (hemicalcium salt) | 0.238 mg., 238 μg. |
| Pyridoxine hydrochloride | 61.5 μg. |
| Thiamin chloride hydrochloride | 0.337 mg., 337 μg. |
| Vitamin B$_{12}$ (Hydroxocobalamin hydrochloride) | 136 μg. |
| Riboflavin | 37.5 μg. |
| Salts (Inorganic) | |
| Calcium chloride | 111 mg. |
| Magnesium sulfate | 120 mg. |
| Dipotassium hydrogen phosphate | 525 mg. |
| Sodium hydroxide | 640 mg. |
| Sodium chloride | 7.01 g. |
| Ferrous sulfate heptahydrate with 1.49 mg. EDTA (Ethylene diamine tetraacetic acid, disodium salt) | 2.78 mg. |

TABLE I-continued

| Other Components | | | |
|---|---|---|---|
| Inositol | 18 mg. | Hepes Buffer | 11.9 g. |
| Choline chloride | 14 mg. | Phenol red | 1.24 mg. |
| Sodium pyruvate | 165 mg. | Antibiotic solution: | |
| Adenine | 1.35 mg. | 100,000 IU penicillin, 100,000 μg. streptomycin 250 μg. amphotericin B (Fungizone) | |
| Mitogen | | | |
| Phytohemagglutinin (PHA) | 2.0 mg. | | |

As previously mentioned and as set forth later herein, in the culture medium of Table I, glucose can be replaced by a substance which can produce glucose as a metabolic product, ferrous sulfate can be replaced by transferrin, ferric ions cannot be used effectively by themselves, except with transferrin, serine can be omitted under certain conditions in making certain tests, and in well nourished individuals only pantothenic acid stores are inadequate for the activation and initial cell divisions of lymphocytes.

The components of the culture medium of Table I can be varied. In general, effective amounts of the components are used and can vary widely for the various nutritional assays and for individual patients. An effective amount of a component, as used herein, is an amount which will obtain a desired response from the patient. Preferably, the amount of the component should not fall substantially below the dose response curve of the particular component for the patient. For most patients and assays the following ranges of components are satisfactory. The precise amounts of the components to provide an effective response can be determined by simple experimentation with the culture medium.

Glucose.—In Table I is indicated the preferred media level of glucose for routine testing, i.e. 720 mg/l. Routine testing can be done with glucose concentration as high as 7200 mg or 7.2 g/l. and as low as 72 mg/l. However, for carbohydrate replacement tests the levels from approximately 8 to 72 mg/l are the most useful for determining the ability of cells to utilize glucose relative to other carbohydrates or to test for substances which spare the amount of glucose needed.

Amino acids.—The preferred levels of amino acids are listed in Table I for routine testing; however, if all of the amino acids are increased in the same amount relative to the concentrations indicated in Table I, useful data can be obtained with no significant decrease in response with a 20 fold increase in the concentrations. At 40 fold, inhibition begins to become apparent and at 60–80 fold, inhibition of response by amino acids precludes useful routine tests. The amount of the amino acids can collectively be decreased slightly and individually can be decreased below the concentration of that indicated by Table I from 0.3 to 0.1 of that level and still provide useful information. For determination of amino acid requirements, the dose response for half-maximal response would usually be in the approximate range of 0.1 times the amount listed in the Table with some in the range of 0.03 times the amount listed in the Table. For test of imbalance, the amino acids have been added at high levels, for example 6–10 times higher than normal blood levels with useful results.

VITAMINS

Pantothenic acid.—This is the only vitamin which is absolutely essential for routine testing of most individuals. Responses can be obtained with as little as about one-twentieth the amount listed in Table I, and the upper limit is open for it is non-toxic even at very high relative levels. Dose-responses which are important are obtained by varying the levels and begin at about 10 μg/l of medium. Optimal response occurs well below the level listed in Table I and the toxicity level is very high.

Riboflavin.—The response of lymphocytes to riboflavin begins to occur significantly at a concentration of 0.001 times that indicated in Table I, and maximal response, which varies for different deficient individuals, occurs between 0.003 and 0.1 times the level indicated in Table I. The level in Table I is used to obtain some indication of abnormal requirements, but useful tests in the range of 0.01 to 0.1 times the level of Table I are obtained. No attempt has been made to find an upper limit for toxicity, but it would be much higher.

Folinic acid.—The lowest useful level of folinic acid to detect responses is in the range of 0.03 to 0.1 times the level indicated in Table I, but in tests in which adenine or serine-glycine interconversion is limiting as much as 10 to 20 times as much folinic acid may be required for an optimal response. Very high levels of folinic acid tend to reduce the response.

Biotin.—The level of biotin which is required for a response is substantially below the level indicated in Table I. In individuals showing a biotin inadequacy, a significant response at levels of 0.01 to 0.03 times that indicated in Table I can be obtained but higher levels are needed to detect abnormal requirements. The upper limit would be relatively high.

Vitamin $B_6$.—In patients with a deficiency of vitamin $B_6$, useful responses can be obtained at levels of about 0.03 to 0.1 the indicated amount in Table I, except where glycine and/or serine is omitted under which conditions at least 10 to 20 times as much as indicated in Table I for the basal medium have been used. The toxic level would actually be much higher.

Vitamin $B_{12}$.—A range of 0.1 to 10,000 μg/l would be required to test all possible conditions.

Nicotinamide, Thiamine.—The toxicities of these have not been determined for an upper limit. In deficient individuals the lower level to show a response would likely be in the range of 0.01 to 0.03 that of Table I.

SALTS

Calcium chloride.—A decreased response is obtained at 0.1 of the level in Table I (i.e., 11.1 mg/l); a near optimal response is obtained at 55.5 mg/l; and for most individuals optimal responses are still obtained at 222 mg/l with some actually requiring this higher amount for an optimal response. At 333 mg/l a decrease in response was obtained with one of four individuals tested. Calcium chloride can be increased about 3 fold of that in Table I without significant inhibition of the response in many individual tests. The upper level at which detrimental effects would be a factor are not too much higher.

Magnesium sulfate.—Lower limit is about 0.1 of the level in Table I. Three times the level indicated in Table I, or 360 mg./l. has been used successfully, and up to 5 fold of that in Table I results in no significant inhibition of the response.

Ferrous sulfate heptahydrate with ethylenediamine heptahydrate.—The lower limit was 0.1 of that indicated in Table I in several patients, with one having a good response at 0.05 times that shown in Table I. Up to three times the level shown in Table I has been used successfully, and ten times might be suitable before toxicity would negate the test.

Transferrin can replace the ferrous sulfate, and 0.3 mg/l is the lower limit with slightly reduced response; up to 30 mg/l showed optimal responses. The upper limit for toxicity has not been determined.

Sodium chloride.—The concentration of sodium chloride is critical. Even 25% increase or decrease can be significantly detrimental to the test.

Dipotassium hydrogen phosphate.—A 4 fold increase decreased the counts from 11,800 to 9,350 which can provide a satisfactory testing result; however, when increased 10 fold of that in Table I, there was an insufficient response.

Sodium hydroxide.—Needed in sufficient amounts to adjust the pH of the medium which can be from pH 6.8 to about 7.6.

OTHER COMPONENTS

Inositol.—A concentration of 0.018 mg/l gives about 70% of maximal response, and 0.18 mg/l gives 90–100% of maximal response. 72 mg/l also gives maximal response, thus toxicity would not occur except at very high concentrations. Since inositol is merely stimulatory, omitting it usually causes only a modest decline in response. In one group of individuals, decreased responses up to 50% occurred, but no decrease was observed with the lymphocytes of some individuals.

Choline.—A concentration of 0.014 mg/l is inadequate; 0.14 mg/l provides almost a maximal response; and concentrations of 1.4 mg/l to 56 mg. provide optimal responses with no significant toxicity for the lymphocytes of most individuals.

Pyruvate.—A suitable range is from about 56 mg/l to about 495 mg/l; 16.5 mg/l is inadequate; 1650 mg/l is toxic.

Adenine.—13.5 mg/l is satisfactory, but 135 mg/l shows toxicity. Low limit is approximately 0.1 times the level of Table I.

PHA.—A suitable range is from 1 mg to 20 mg per liter, but the limits vary with the lymphocytes of individual patients.

It is possible to omit one of the vitamins entirely, except pantothenic acid; for example, nicotinamide can be omitted without significantly affecting the response of a large number of patients. Thus, such a medium is successful except for rare patients.

A single amino acid, such as arginine, or a small group of amino acids, can be increased to high levels without significantly affecting the test for a large proportion of patients. The minimal medium, as set forth in Table I, has proved most successful in ranges of 0.3 to 3 times the level of amino acids indicated for the basal test medium.

There is a definite minimum requirement for each amino acid for lymphocytes cultured in the minimal medium of Table I. This limit as well as the upper limit depends on the composition of the medium since the lymphocyte response is frequently the result of a ratio of concentrations rather than a finite concentration of components. This is a result of mutual antagonisms and varies with different patients, as does the minimum requirement.

Enough mitogen should be present to provide maximum stimulation for the number of cells being tested, enough buffer should be present to maintain the pH from about 6.8 to 7.8, enough phenol red should be present to serve as a pH indicator, and sufficient antibiotic should be present to suppress contamination of the culture medium.

The foregoing amounts and ranges provide effective functioning for the respective components of the culture medium.

SEPARATION OF LYMPHOCYTES

The lymphocytes may be separated from blood samples in any desired and preferred manner. The following is an example of how the lymphocytes can be separated from blood.

Blood samples are collected in sterile, heparinized, 10 ml. Vacutainer tubes and kept at room temperature for no longer than 30 minutes. The samples are diluted 1:2.4 with phosphate buffered saline. The diluted blood (8 ml.) is carefully layered onto 3 ml. of Histopaque (Ficoll and sodium diatrizoate compound obtained from Sigma Chemical Co.) contained in appropriate tubes. Twenty minute centrifugation at 2000 rpm in a NIEC clinical centrifuge separates the erythrocytes from the lymphocytes, the latter remaining in a layer on top of the Histopaque. This layer contains primarily lymphocytes.

The lymphocytes are extracted from the tubes using sterile Pasteur pipettes. Approximately 0.5–2.5 ml. of extracted lymphocytes are placed in 15 ml. Corning plastic centrifuge tubes containing about 6 ml. of medium salts, or other appropriate solution. (Generally, 6 Histopaque tubes are required for 20 ml. blood, and the lymphocytes from these tubes are placed in 4 Corning tubes). The centrifuge tubes are then inverted several times to aid in washing the cells after which they are centrifuged at 1700 rpm for 10 minutes. The supernatant is discarded and the cells in each tube are resuspended in approximately 1 ml. of medium salts using gentle aspiration with a sterile Pasteur pipette. The contents of all four tubes are combined into one tube, the remaining three tubes are rinsed with medium salts and the rinse is transferred by means of Pasteur pipette to the lymphocyte suspension. The tube containing the lymphocytes is inverted several times, then centrifuged at 1700 rpm for 10 minutes and the supernatant is discarded.

The lymphocyte pellet is resuspended in 3 ml. of medium salts in the manner just described. The cells are now counted in a Coulter Counter as follows: 20 μl. of the suspension is added to 10 ml. of Isoton in a plastic Coulter Acuvette and 1 drop of Zapoglobin (Coulter Diagnostics) is added to lyse the cell membranes so that the nuclei can be counted. The solution is gently swirled and counted three times on the Coulter Counter. Based on the average of the three values, the lymphocyte solution is diluted to a concentration of 3 million cells per ml. with medium salts and recounted. This lymphocyte suspension is then used to inoculate the assay.

The lymphocytes can be isolated from blood according to other methods in the art. For example, the blood obtained from the test person can be rendered non-coagulating in the usual manner, for example, by adding an anti-coagulant such as heparin, and subsequently the lymphocytes are recovered therefrom by known methods, for example, by introducing the blood sample into a column charged with glass beads. Adherent cells adhere to the beads. The lymphocytes can be recovered from the eluate by gradient centrifugation. Alternatively, an adsorption of adherent cells on glass beads may be dispensed with so that gradient centrifugation can be directly employed.

Further suitable processes for obtaining lymphocytes are described, by way of example, in the following references: Johnson, G. J. and Russel, P. S., Nature 208, pp. 343 (1965); Boyum, A., Scand. J. Clin. Lab. Invest. Suppl. 77 (1966); Oppenheimer, J. J., Leventhal, P. G., Hersh, E. M., Journal Immunology 101, pp. 262–270 (1968); Twomey, J. J., Sharkey, O., Journal Immunology 108, pp. 984–990 (1972).

All of the lymphocytes, which have been obtained and purified by one of the above methods, may be diluted to an appropriate concentration and this suspension is then used to inoculate the culture medium.

LYMPHOCYTE ASSAY

In general, the assay comprises inoculating the culture medium with the test lymphocytes, incubating the inoculated culture medium, harvesting the incubated cultures, and measuring the response, such as activation and initiation of growth, of the lymphocytes.

The following is an example of a presently preferred lymphocyte assay.

Previously sterilized (by ethylene oxide) 12×75 mm. polystyrene tubes with caps (Scientific Products) are used in this assay procedure. One milliliter of the culture medium is added to each tube. Where necessary, variable supplements up to 30 μl. may be added to each tube, or a smaller volume of an appropriately higher concentration of the medium can be added to the tubes and supplements then added to make a final volume of 1 ml. The assay is then inoculated with 50 μl. of the diluted lymphocyte suspension (150,000 lymphocytes).

Incubation—The culture tubes are placed in stainless steel racks and incubated for 4 days at 37° C. in a 5% carbon dioxide atmosphere saturated with water vapor. On the fourth day they are removed and placed in a 37° C. water bath for pulsing with 0.1 μCi per tube of $^3$H-thymidine which has a specific activity of 300 μCi/m-mole. The cultures are then replaced in the incubator for 23–25 hours before harvesting takes place. Other times before harvesting can be used, e.g. 8 hrs., with similar results relative to controls.

Harvesting—The cultures are harvested on a Millipore sampling manifold using 0.45 μm. filter papers which are capable of filtering out nucleic acids. The caps are removed from the tubes, the tubes are placed on ice and subsequently mixed well on a Vortex mixer. The filter papers, once positioned, are moistened with ½ strength phosphate buffered saline which is used throughout the harvest. The first 12 tubes are again mixed on the Vortex mixer, then filled ¾ full with the same saline solution. They are sequentially poured on the 12 filters of the sampling manifold. Each tube is washed twice with the saline solution and the washes are also poured on the filters. Then approximately 5 ml. of the saline solution is poured on each filter for the final wash. This procedure is repeated, 12 tubes at a time, for the remainder of the assay.

The filter papers are dried for 5 minutes in a drying oven at 120° C. and then placed in counting vials containing 10 ml. of a toluene-PPO scintillation cocktail (20 g. PPO per 4 l toluene). The vials are counted in a Beckman LS 250 liquid scintillation counter.

The above assay procedure can be modified, for example, by carrying out the assay in 0.2 ml. of culture medium in wells of microassay plates, e.g. Corning or Falcon, instead of 1 ml. of culture medium in culture tubes. The same culture medium and the same concentration of supplements are used. Supplements are first placed in appropriate wells in 2 μl. amounts rather than the usual 10 μl. since the final volume will be 1/5 that of the larger cultures. The lymphocytes are washed in medium salts as usual, but after the final wash they are then suspended in the same type of medium that is to be put in the wells at a concentration of 150,000 cells/ml. This suspension is pipetted into each well, 0.2 ml/well, giving a total volume of 0.22 ml. and a final cell concentration of 30,000/0.22 ml. The plates are then incubated as usual; 10 μl. rather than 50 μl. of the same solution of $^3$H-thymidine (specific activity 300 μCi/mmole) is used to pulse on the fourth day. Harvesting on the fifth day or an appropriate time after pulsing with thymidine is done using a Brandel M-12 cell harvester and Brandel filter paper rather than the Millipore filter paper and sampling manifold used for the 1 ml. cultures.

The above procedures represent two types of culture conditions, but many other variations are possible in the procedure to achieve the basic concept of assessment of nutritional needs of an individual and to detect differences in requirements based upon biochemical individuality as well as ordinary deficiency states.

For determining abnormal requirements for essential amino acids, sensitivity to detrimental effects of higher concentrations of amino acids (e.g., amino acid imbalance) and inability to synthesize adequate amounts of non-essential amino acids, a routine determination can be made with supplements of each one of all of the amino acids—including those not in the medium—at levels which approximate an average blood concentration and at the same time at levels which are significantly higher than the average concentration. Detrimental effects of elevated concentrations of an amino acid can frequently be overcome by additional supplements of another amino acid(s) or of certain vitamins.

An abnormal requirement for an amino acid can be detected by preparing media as described except that the one amino acid for which the quantitative requirement is to be determined is omitted, and is added over a range of concentrations to separate tubes to obtain a dose-response curve. Alternatively, one limiting concentration of the amino acid could be used by comparing the response of the limiting concentration in lymphocytes of the patient with the range of responses of lymphocytes of a group of subjects to that concentration of the particular amino acids. Two different concentrations could also be used to provide additional information without obtaining the entire dose-response curve. In selecting these concentrations to be used in testing, the following concentrations of amino acids as set forth in Table II provide a response which is limited by the specific amino acid. A half-maximal response can be obtained at concentrations near those listed in Table II.

TABLE II

| | Concentration in mg/liter |
|---|---|
| Arginine | 0.5 |
| Glycine | 0.25 |
| Histidine | 0.25 |
| Isoleucine | 0.25 |
| Leucine | 0.25 |

TABLE II-continued

| | Concentration in mg/liter |
|---|---|
| Lysine | 0.8 |
| Methionine | 0.2 |
| Phenylalanine | 0.2 |
| Serine | 0.4 |
| Threonine | 0.2 |
| Tyrosine | 0.2 |
| Tryptophan | 0.1 |
| Valine | 0.25 |
| Glutamine | 15.0 |
| Cysteine | 5.0 |

A single specific concentration approximately at the half-maximal response level can provide information on abnormal requirements with minimal testing. A two point response could be obtained by a slightly lower and slightly higher concentration, e.g., $\frac{2}{3}$ and 4/3 of the above amounts giving half-maximal response, or a complete dose-response curve could be obtained with a multiple group of concentrations in this general range of concentrations.

An abnormal requirement for minerals, such as calcium or magnesium, and sensitivity to detrimental effects of higher concentrations of minerals, can similarly be determined.

Omission of B-vitamins, one at a time, from the medium—or in groups, such as omission of vitamin $B_{12}$ and folinic acid—usually does not result in a decreased response except in the case of pantothenic acid. Thus a decreased response in the case of vitamins other than pantothenic acid is an indication of a deficiency, an abnormal requirement for the vitamin, or a defective storage of the vitamin. The levels of response in the absence of pantothenic acid can also be similarly utilized in the assessment of nutritional status of pantothentic acid. The decreased response on addition of vitamin antagonists, e.g., desthiobiotin as an inhibitor of biotin utilization, can be used as a measure of the adequacy of a vitamin for the inhibited system. This can be more specific than the vitamin requirement with respect to certain vitamins.

Using well known methods to remove any trace elements which may be contaminating medium ingredients makes it possible to detect trace element deficiencies and abnormal requirements for such nutritional factors. Sensitivity to drugs and various toxic substances and the interaction of these in altering nutritional requirements can be tested as well.

Certain culture medium components can be omitted by increasing other components. For example, serine and glycine can be omitted from the culture medium in the lymphocyte assay of many individuals by increasing the concentration of folinic acid and of vitamin $B_6$ (pyridoxine) several fold. Such tests determine the ability of an individual to synthesize serine. In the absence of supplements of folinic acid and vitamin $B_{12}$ the ratio of the response to glycine alone in comparison to serine alone is greater than 1 in the lymphocytes of most individuals. On the other hand, with lymphocytes of pernicious anemia patients the response to serine exceeds the response to glycine under these conditions.

The ability of an individual to synthesize inositol or choline can be determined by omission of these components from the culture medium. For example, the lymphocytes of some individuals cannot synthesize sufficient inositol while the lymphocytes of most individuals can synthesize a substantial part of their inositol requirement. Variation in the ability to synthesize choline is observed in different individuals. 2-Dimethylaminoethanol can significantly replace choline, and the extent of this replacement can be used to determine the ability of lymphocytes of individuals to carry out the synthesis of choline from this intermediate.

Omission of adenine allows a determination of the factors affecting purine synthesis in an individual. For example, the requirements for folinic acid, glycine and glutamine are altered under these conditions for various individuals. 5-Amino-4-imidazolecarboxamide or its ribosyl derivative significantly replaces adenine in stimulating lymphocytes. Such a supplement not only provides information concerning which stage or purine biosynthsis is limiting, but also allows a determination of the folinic acid requirement for the last insertion of formate into the purine nucleus.

For broad surveys of nutritional status, variations in nutrient interrelationship, drug and nutrient sensitivities, etc., the assay with a small volume, e.g. 0.2 ml. cultures requiring an inoculum of about 30,000 lymphocytes, can involve as many as 750 individual tests which, if carried out in triplicate, can allow 250 different test variations for lymphocytes from about 20 ml. of blood. This permits a very broad survey of the deficiencies or abnormal requirement of nutrients, sensitivity to nutrient imbalances, sensitivity to toxic effects of nutrients, drugs and a wide variety of substances, and many biosynthetic capabilities for each individual.

In the culture medium, approximately one day is required for activation and an exponential response curve is obtained for about the next four days after which the response declines unless the cells are separated and new medium added. An initial incubation in a deficient medium allows depletion of certain components, and a subsequent test can be used to amplify certain deficiencies. Cells activated in the presence of specific nutrients such as pantothenic acid will concentrate sufficient amounts of these components so that their presence is not essential in a subsequent incubation to obtain a maximal response.

Glutamic acid, aspartic acid, asparagine, alanine and proline can be omitted from the culture medium. Of the remaining 15 amino acids essential for protein synthesis, glycine and serine can be omitted under certain conditions for lymphocytes from some individuals but are stimulatory to others.

Among B-vitamins only pantothenic acid was absolutely required for essentially optimal response in many well-nourished individuals; however, riboflavin and vitamin $B_6$ were frequently found to be stimulatory, and other vitamins showed stimulatory effects with decreasing frequencies. These frequencies correspond rather closely with the frequencies of vitamin deficiencies determined by various methods. It thus appears that except for pantothenic acid, the B-vitamins are normally stored in lymphocytes in adequate amounts for activation and initiation of growth. The appearance of a stimulatory response indicates that the lymphocytes were deficient in regard to enzyme content and/or storage of the particular vitamin or had abnormal requirements for the vitamin. Since lymphocytes are inactive and do not take up vitamins such as folic acid until activated by a mitogen, these cells apparently carry the nutritional history of the individual possibly from the time of their development from active bone marrow cells. This is a great advantage in the assessment of nutritional status but not in evaluation of the results of nutritional therapy.

Lymphocytes are very sensitive to riboflavin deficiencies. There is a correlation between the increase in a number of patients with lymphocytes stimulated by riboflavin (as well as the magnitude of the stimulation) with decreases in levels of urinary riboflavin excretion.

There is also a similar correlation between decreased erythrocyte glutamate-oxalacetate transaminase levels and the number of patients with decreases in the response of their lymphocytes to omission of vitamin $B_6$. This would be expected since aspartic acid and asparagine are omitted from the lymphocyte medium. Also, the erythrocyte level of this transaminase has been used to indicate the level of vitamin $B_6$ intake since supplements of vitamin $B_6$ markedly increase the amount of this enzyme.

Such data indicate a relationship between intake level and the potential for a cellular deficiency of the vitamin affecting the lymphocyte. However, there is a possibility that very high intake levels can exert a repression in storage mechanisms. If so, a lymphocyte deficiency associated with high urinary output and a normal response curve of the vitamin would indicate the possibility that a reduced intake level would be beneficial. Two such cases have been found.

In order to study the overall problems associated with an ultimate evolution of the methods being developed, patients with many types of disorders have been included during this phase of the study.

When glucose is omitted from the culture medium in the assay, the ability of other carbohydrates to replace glucose can be used to determine whether or not an individual has the ability to utilize effectively these carbohydrates. For example, in galactosemia there is an inability to metabolize galactose derived from lactose, and this metabolism involves the conversion of galactose to glucose. Inability to metabolize galactose properly can lead to a number of defects including mental retardation, cataracts, etc. Also, the susceptibility to inhibition by excess galactose can be determined. This may have importance in the development of cataracts in later life.

Carbohydrates other than galactose, e.g., mannose, can be similarly tested for ability to be utilized in place of glucose and for their toxic effects in each individual, for example, the abnormal susceptibility of an individual to inhibition by ribose, an essential carbohydrate for nucleic acid biosynthesis. The procedure in each instance of carbohydrate testing is to determine the ability of the carbohydrate to replace glucose and to determine the susceptibility of the lymphocytes to inhibition of growth by the carbohydrate.

Treatment in the case of a galactose utilization defect would be to avoid foods containing its sources, e.g., lactose in milk products. In other cases, such as abnormal ribose inhibition, the lymphocyte assay can determine which nutrients or inter-related biochemicals have the ability to reverse the inhibitory effect.

Insulin deficiency in an individual can be detected by culturing lymphocytes of the individual in medium containing sufficient glucose for an optimal response. For example, insulin deficiency can be detected by determining the effect of 0.01 units per ml of insulin on the response to 0.01, 0.03, 0.1 and 1.0 times the normal medium concentration of glucose. At low levels of glucose, e.g. 0.03 of the normal medium concentration, insulin exerts a growth effect which is interpreted to be a "sparing effect" upon the glucose requirement since in most individuals no substantial effect of insulin is observed at 0.1 or 1.0 times the normal media concentration of glucose. However, in patients with insulin insufficiency, the added growth stimulation by insulin persists even at the higher levels of glucose. Two patients who were subsequently shown by glucose tolerance tests to be diabetic were detected in this manner.

From the results obtained during the course of the development of the medium, it was discovered that deficiencies in storage of vitamins and, potentially, trace elements, abnormal requirements for and sensitivities to imbalances of nutrients such as amino acids, abnormalities in purine and pyrimidine biosynthesis, and many other aspects of variations in intermediary metabolism could be detected through individual lymphocyte cultures. It is currently feasible with 0.2 ml. cultures of lymphocytes to obtain triplicate determinations with over 200 variations in culture conditions from a 10 to 20 ml. blood sample in a survey of the nutritional status of an individual.

During the course of the development of the culture medium necessary for this method of assessment of individual nutritional status, a wide variety of controls and patients with various diseases have been involved in order to be able to determine the extent ot the variations in responses. As a result, there is some indication that the method can be used as a useful clinical procedure.

EXAMPLE 1

One of the first cases benefitting from participating in the program of developing the lymphocyte medium was a patient who had a long medical history of lassitude, intense parethesia, muscle pain, mild depression and extreme anxiety. After exhausting medical resources for alleviation of his illness, consultation with a nutritionist resulted in his referral to our program. The lymphocyte assay revealed approximately a 50% decrease in growth without biotin supplements contrasted to no decrease in most normal subjects. Further investigation revealed that the patient was fond of a drink containing raw egg white which he used daily. This coupled with consumption of eggs barely heated for breakfast, undoubtedly places this subject in the category of avidin-induced biotin deficiency. Injections of 300 g. of biotin for 5 days alleviated the patient's severe symptoms, and he has since been maintained on oral biotin.

EXAMPLE 2

A patient, A. L. W., age 86, with severe mental deterioration was similarly found to be biotin deficient as well as riboflavin deficient. Treatment with biotin and riboflavin resulted in an ability to communicate which was not possible before. Urinary output of biotin and riboflavin confirmed the deficiency state. Also, administration of the two vitamins eliminated the urinary excretion of a component(s) with an offensive odor. On the basis of the lymphocyte test, with confirmation in many cases with urine analyses, it appears that biotin deficiencies occur, particularly in the elderly, far more frequently than had been anticipated.

EXAMPLE 3

H. M., a 5 year old girl, had a lack of muscle tone, inability to balance with eyes closed, difficulty in holding her head erect, abnormal eye movements in response to a rotation test, and a physical therapist evaluation of physical problems in an otherwise exceptionally bright child. Her lymphocyte test showed a decrease to 57% of control on omission of riboflavin, which was the outstanding difference from normal subjects. Administration of 10 mg. daily of riboflavin each morning caused a remarkable change not only in normal eye movements in response to the rotation test for the first time in a year of physical therapy, but in behavior toward exercise routines and participation in play. Her parents considered her to be normal again, and the physical therapist considered the change very exceptional. In this little girl (H. M.), urinary excretion of riboflavin was in the low risk level at the time of the initial lymphocyte test. Thus the lymphocyte test detected an abnormal requirement for riboflavin, and it appears likely that continued experimentation will allow actual physical data to verify the rapid response to supplementation and to withdrawal of supplementation.

EXAMPLE 4

In studies of the requirements of lymphocytes for vitamin $B_{12}$ and folic acid, it was necessary to develop additional techniques because these vitamins are involved in the formation of thymidylic acid which affects the thymidine incorporation. Vitamin $B_{12}$ has some activity in allowing homocysteine to replace methionine in the activation and growth of lymphocytes. However, in a study of an untreated pernicious anemia patient, it was apparent that the pernicious anemia patient could utilize serine for the formation of glycine but could not form adequate amounts of serine from glycine. These results indicate that the pernicious anemia patient had a deficit of $N^{5,10}$-methylenetetrahydrofolates but had adequate amounts of tetrahydrofolates while the "normal subject" utilizing glycine but not serine effectively had adequate amounts of $N^{5,10}$-methylenetetrahydrofolates but a deficit of tetrahydrofolates. Many years ago it was shown that the $\beta$-carbon of serine but not formate could be utilized in the biosynthesis of thymidine of DNA in pernicious anemia patients. Thus, vitamin $B_{12}$ deficiency greatly affects the amount of the single carbon unit in the methylene state attached to reduced folate co-enzymes.

Vitamin deficiencies in lymphocytes can be traced to specific reactions. By eliminating glycine, pyridoxine, folinic acid and vitamin $B_{12}$ from the medium, the conversion of serine to glycine requiring pyridoxal phosphate and a tetrahydrofolic acid can be made the limiting reaction for activation and initiation of growth of lymphocytes. A broad range of variation in the amount of tetrahydrofolic acid derivatives available within lymphocytes exists from patient to patient. From a study of about fifty patients, it was found that normal individuals do not carry folic acid derivatives in this form sufficient for forming adequate amounts of glycine from serine; however, a pernicious anemia patient, L.A., does carry available stores supplying adequate amounts of the folic acid receptor for the single carbon unit. Pyridoxine is generally present in adequate amounts for this reaction even though it may not be at adequate levels for other systems, but lymphocytes from an occasional patient, e.g., S.B., do show a significant decrease in the absence of pyridoxine when adequate folinic acid is present. The two sets of data indicated for S.B. were determined several weeks apart to be certain of the deficit of vitamin $B_6$ under these conditions which had not been observed in the first thirty of this group of patients.

EXAMPLE 5

A rather broad variation exists in the ability of lymphocytes to synthesize glycine and serine. Invariably, folinic acid and pyridoxine are required for maximal response in the absence of glycine and serine in the medium, but the cells of one individual were able to attain 70% of the control response in the absence of these vitamins. In another case, N.B., the ability to dispense with serine and glycine was minimal with only a 24–27 percent of control response even in the presence of pyridoxine and folinic acid supplement. This patient, N.B., responded to serine supplements in a beneficial way.

EXAMPLE 6

One area of exploration and evaluation with the lymphocyte assay has involved children with mental disorders. In the group studied, two autistic-like individuals fit the diagnostic category of Childhood Onset Pervasive Developmental Disorder.

A. is an 8 year old male who had phobic fear of lightning, delayed speech development, bizarre behavior, and general immaturity. He was very small and immature for his age; he was unable to play alone or with the interviewer. He was very anxious not to be separated from his mother, and his only use of language was to repeat exactly the words of the interviewer. The lymphocyte assay showed a 20% decreased response upon the absence of pyridoxine, and an 18% decrease in omission of folic acid which was altered by vitamin $B_{12}$ omission. The ratio of the response of glycine relative to that of serine in a medium from which serine, glycine, vitamin $B_{12}$ and folic acid were omitted was 0.76 which corresponds closely to the ratio obtained with pernicious anemia patients. On the basis of the lymphocyte responses, supplements of 100 μg. of vitamin $B_{12}$, 25 mg. of pyridoxine, 0.3 mg. of folic acid and a multivitamin preparation providing the minimum daily requirements of other vitamins were instituted. Additionally, he was placed in weekly individual psychotherapy. His progress has been remarkable. He has developed, with the assistance of his therapist, play skills. He separates from his mother with little anxiety, and most remarkably communicates verbally in a spontaneous and appropriate manner. Underlying these changes is a clear developmental progression. At the time of initial evaluation, no such progress would have been predicted based on experience with numerous patients presenting similar cases.

S., the eldest of three siblings, when first seen for for psychiatric evaluation at age 8, spent much of his time anxiously rolling a stick between his hands, avoided eye contact, and when aroused flapped his arms and hands in a bizarre manner. At home, he was described as having "retarded comprehesion", and his parents felt that they "just can't get through to him." He became very upset when anything was changed in his room, had temper tantrums during which he would bang his head on the floor, and always wanted to take the same route while riding in the car. Placed in a class for emotionally disturbed youngsters, he was seen by his teacher as performing well below his capability, primarily because of his uncontrollable behavior. Psychiatric diagnosis was that of childhood psychotic disorder (i.e., autism, schizophrenia, pervasive development disorder) in an otherwise bright child. During two years of regular psychotherapy with subsequent initiation of parental therapy, there were alternating periods of progression and regression not unusual for such cases. In addition, phenothiazines (Stelazine, Mellaril) were employed to gain enough behavioral control of S. to function in school.

At this point, the lymphocytes of the patient were tested and found to be 35% deficient in vitamin $B_6$ and 34% deficient in riboflavin, and also required higher than normal amounts of glutamine for maximal responses.

S.'s diet was supplemented with 25 mg. of riboflavin, 25 mg. pyridoxine and 2 g. of glutamine daily. Over the next four months, S. was seen in weekly therapy, his parents were also seen in weekly therapy, and he continued in special education classes. Within 4–6 weeks after the initiation of the supplements, S.'s parents noted that the phenothiazine which he had been taking regularly with good results was causing side-effects normally associated with excessive dosage. As instructed, they gradually reduced The dose until it was finally discontinued. Over this time, no deterioration in his behavior was noted (i.e., he did not revert to his pre-medication behavior). His teachers also reported continual improvement in his behavior. At the same time, S.'s therapist noted changes, at first in behavior but also in the level of personality development. Briefly, before the supplements were initiated, S. had exhibited behavior seen normally in infants.

S.H., age 6, was diagnosed as atypical organic brain syndrome with mild metal retardation, IQ high 60's. He was maintained on therapeutic levels of dilantin and Mysoline but was still experiencing about 8 to 10 seizures daily. The lymphocyte response indicated riboflavin deficiency in the cells, a higher than normal requirement for glutamine and an unusual sensitivity to inhibition by glycine and alanine. Administration of riboflavin (25 mg. daily) and glutamine (2 g. daily) was initiated. At 10 weeks, the type of seizure changed to primarily psychomotor and petit mal seizures, and at 16 weeks he was seizure-free.

Accordingly, the present invention is well adapted and suited to attain the objectives and ends and has the advantages and features mentioned as well as others inherent therein.

While presently preferred embodiments of the invention have been given for the purpose of disclosure, changes can be made therein which are within the spirit of the invention as defined by the scope of the appended claims.

What is claimed is:

1. A cell culture medium effective for lymphocyte assay of nutritional and biochemical status of cells from human beings comprising,
   a buffered, serum-free solution containing the following ingredients in a range of minimal amounts effective for a maximal dose response to amounts less than inhibitory and toxic concentrations thereof,
   a carbohydrate selected from the group consisting of glucose and a compound biologically capable of producing glucose in the cells,
   a biologically usable form of pantothenic acid,
   choline or a biological usable form of a substance capable of producing choline in the cells,
   inorganic ions comprising chloride, phosphate, calcium, magnesium, potassium, sodium, and iron in a biologically utilizable form,
   deionized water, and a mitogen in an amount effective to stimulate the lymphocytes being assayed, said buffered, serum-free solution having a pH from about 6.8 to 7.6, said cell culture medium characterized by being effective to determine nutritional and biochemical deficiencies, inadequacies, and imbalances of the lymphocytes when supplemented with a nutrient supplement selected from the group consisting of biological utilizable forms of amino acids and vitamins, the nutrient being tested for being omitted from or being present in limiting or inhibitory amounts in the nutrient supplement.

2. A cell culture medium effective for lymphocyte assay of nutritional and biochemical status of cells from human beings comprising, a buffered, serum-free solution containing the following ingredients in a range of minimal amounts effective for a maximal dose response to amounts less than inhibitory and toxic concentrations thereof, a carbohydrate selected from the group consisting of glucose and a compound biologically capable of producing glucose in the cells, a biologically usable form of pantothenic acid, choline or a biological usable form of a substance capable of producing choline in the cells, inorganic ions comprising chloride, phosphate, calcium, magnesium, potassium, sodium, and iron in a biologically utilizable form, deionized water, a mitogen in an amount effective to stimulate the lymphocytes being assayed, said buffered, serum-free solution having a pH from about 6.8 to 7.6, said cell culture medium characterized by being effective to determine nutritional and biochemical deficiencies, inadequacies, and imbalances of the lymphocytes when supplemented with a nutrient supplement selected from the group consisting of biological utilizable forms of amino acids and vitamins, the nutrient being tested for being omitted from or being present in limiting or inhibitory amounts in the nutrient supplement, and the vitamins are selected from the group consisting of biotin, folinic acid or a biologically usable form of folic acid, nicotinamide or nicotinic acid, riboflavin, thiamin, vitamin $B_6$, and vitamin $B_{12}$, and compounds capable of producing them in the cells, and the amino acids or the compounds biologically capable of producing the amino acids comprise L-arginine, L-cysteine, L-glutamine, glycine, L-histidine, L-isoleucine, L-leucine, L-lysine, L-methionine, L-phenylalanine, L-serine, L-threonine, L-tryptophan, L-tyrosine, and L-valine, the amino acids being present as a group, each in an amount not exceeding inhibitory concentrations.

3. The cell culture medium of claims 1 or 2 where, the cell culture medium is supplemented at concentrations eliciting approximately a maximal response with one or more stimulatory nutrients selected from the group consisting of pyruvate, adenine, and inositol or compounds capable of producing them within the cells.

4. The cell culture medium of claims 1, 2 or 3 where, each amino acid of the amino acid supplement being present in about the minimum concentration effective for a maximal response of the cells except the amino acid being tested.

5. The cell culture medium of claims 1, 2, 3 or 4 where, the medium is free of either or both serine and glycine, and in which an effective concentration for cell response of either or both vitamin $B_6$ and a utilizable form of folic acid are included in the culture medium.

6. The cell culture medium of claims 1, 2, 3, 4 or 5 where the medium is free of one of pantothenic acid and choline, the cell culture in said medium being effective to determine nutritional deficiencies and abnormal requirements when supplemented with response limiting amounts of pantothenic acid and choline of which the culture medium is free.

7. The cell culture medium of claims 1, 2, 3, 4 or 5 where, the cell culture medium is free of at least one of the inorganic ions, the cell culture in said medium being effective to determine deficiencies or abnormal requirements when supplemented with growth limiting amounts of the inorganic ion not present in the cell culture medium.

8. A method of determining deficiencies or storage inadequacies of essential nutrients in an individual comprising, inoculating the cell culture medium of claims 1, 2, 3, 4, 5, 6 or 7, free of the nutrient being tested for with lymphocytes of the individual, incubating the inoculated cell culture medium for a time sufficient for depletion of the nutrient being tested, and comparing the response of the lymphocytes of the individual with a response of the lymphocytes in the same medium supplemented with the nutrient being tested, and with responses of lymphocytes of control individuals.

9. A method of determining abnormal quantitative nutritional requirements for specific required nutrients in an individual comprising, inoculating the cell culture medium of claims 1, 2, 3, 4, 5, 6 or 7 with lymphocytes of the individual, the culture medium having limiting concentrations of the nutrient being tested, incubating the inoculated cell culture medium, and comparing the response of the lymphocytes with an average response of lymphocytes from a control group of individuals.

10. A method of determining sensitivities of an individual to detrimental effects or imbalances of nutrients, metabolic intermediates and their products and other blood components including drugs comprising, inoculating with lymphocytes of the individual the cell culture medium of claims 1, 2, 3, 4 or 5 supplemented with at least one of the nutrients, metabolic intermediates and their products, or other blood components including drugs at concentrations equal to or higher than normal blood levels, incubating the inoculated cell culture medium and comparing the response of the lymphocytes with the response of the lymphocytes in a medium free of the supplemented nutrients, metabolic product or other blood component including drugs or in the case of a required component of the medium, in a medium containing the minimal amount of the required component eleciting a maximal response of the cells.

11. A method of determining deficiencies or abnormal storage of essential nutrients or metabolic intermediates of an individual comprising, inoculating the cell culture medium of claim 1 2, 3, 4, 5, 6, or 7, containing a metabolic antagonist of the nutrient or a metabolic intermediate or its product at a concentration sufficient to cause a defined inhibition of cell response, incubating the inoculated cell culture medium, and comparing the response of the cells at different concentrations of nutrient, metabolic intermediate or the product being tested with analogous responses of cells obtained from a control group of individuals.

12. A method of determining in an individual the nutritional need for supplements of essential biochemical intermediates or their products usually synthesized in adequate amounts by most individuals, inoculating the cell culture medium of claims 1, 2, 3, 4 or 5, supplemented with at least one of the essential biochemical intermediates or products of a group of such biochemical intermediates or products with lymphocytes of the individual, incubating the inoculated cell culture medium, and comparing the response of the lymphocytes to the response of the lymphocytes cultured in the cell culture medium free of the essential biochemical intermediate or the group of such biochemical intermediates or their products.

13. A method for determining the effectiveness of glycolysis in an individual comprising, inoculating the culture medium of claims 1, 2, 3, 4 or 5, free of pyruvate with lymphocytes of the individual, incubating the inoculated culture medium, and comparing the response of the lymphocytes with the response of the lymphocytes in the cell culture medium containing pyruvate as a determination of the ability of the individual to metabolize glucose.

14. A method of determining the ability of an individual to synthesize one of inositol and choline comprising, culturing cells in the culture medium of claims 1, 2, 3, 4 or 5, free of one of inositol and choline inoculated with lymphocytes of the individual, and comparing the response of the lymphocytes with a response of lymphocytes in the cell culture medium containing both inositol and choline as a determination of the ability of the individual to synthesize inositol or choline.

15. A method of determining the ability of an individual to synthesize purines comprising, culturing cells in the cell culture medium of claims 1, 2, 3, 4, or 5, free of purines inoculated with lymphocytes of the individual, and comparing the response of the lymphocytes to the culturing of the lymphocytes in the cell culture medium in the presence and in the absence of precursors of purines, in the presence and in the absence of one or more B vitamins, and in the presence and absence of a utilizable source of purines.

16. A method of determining the ability of an individual's lymphocytes to synthesize stimulatory components comprising, inoculating the cell culture medium of claims 1, 2, 3, 4 or 5, free of a stimulatory compound with and without additions of their precursors and vitamins involved in biosynthesis, incubating the inoculated cell culture medium, and comparing the response of the lymphocytes with the response of the lymphocytes in a medium containing effective amounts of the stimulatory component as a determination of the ability of the individual to synthesize the stimulatory component.

17. A method of determining the ability of an individual to replace glucose with other carbohydrates comprising, culturing lymphocytes of the individual in the culture medium of claims 1, 2, 3, 4, or 5, in which a carbohydrate being tested is substituted for or partially substituted for glucose, and comparing the response of the lymphocytes to the response of lymphocytes cultured in the cell culture medium containing glucose without the substitute carbohydrate.

18. A method of determining the ability of an individual to synthesize at least one or both of glycine and serine comprising, culturing the medium of claims 1, 2, 3, 4, or 5, with lymphocytes of the individual, the medium containing at least one or both of a biologically utilizable form of folic acid and vitamin $B_6$ and free of at least one or both of glycine and serine, and comparing the response of the lymphocytes to a response of the lymphocytes in the cell culture medium containing the nutrient supplements of these amino acids and vitamins.

19. A method of determining insulin insufficiency in an individual comprising, culturing cells in the cell culture medium of claims 1, 2, 3, 4 or 5 with lymphocytes of the individual, and measuring the response of the lymphocytes to the culturing in the presence of insulin thereby effecting an increased response as an indication of whether there is such an insulin deficiency or abnormal insulin response in the individual.

20. A method of identifying nutritional factors or biochemical intermediates which overcomes detrimental effects of nutrients, biochemical intermediates or their products, and other blood components including drugs in an individual sensitive to such detrimental effects comprising, inoculating the cell culture medium of claims 1, 2, 3, 4, or 5 containing at least one of the nutrients, biochemical intermediates or products or other blood components including drugs at a concentration having a detrimental effect on the cell response, incubating the inoculated cell medium, and comparing the response with that in the same medium supplemented with a source of the substance suspected to affect the detrimental effect of the nutrient, biochemical intermediate or its product or other blood component including the drug being tested.

* * * * *

UNITED STATES PATENT OFFICE
CERTIFICATE OF CORRECTION

Patent No. 4,499,064                    Dated February 12, 1985

Inventor(s) William Shive

It is certified that error appears in the above-identified patent and that said Letters Patent are hereby corrected as shown below:

Column 3, line 6, change "mine" to --min--.

Column 3, line 32, change "phytohemogglutinin" to --phytohemagglutinin--.

Column 4, line 9, change "lymphycytes" to --lymphocytes--.

Column 4, line 59, after "0.39" insert -- g.--.

Column 5, line 5, change "$Na_2HOP_4 \cdot 7H_2O$" to --$Na_2HPO_4 \cdot 7H_2O$--.

Column 12, line 18, change "$\frac{2}{3}$" to --2/3--.

Column 13, line 16, change "biosynthsis" to --biosynthesis--.

Column 18, line 30, change "metal" to --mental--.

Column 20, line 67, change "eleciting" to --eliciting--.

Column 21, line 4, change "claim 1 2," to --claims 1, 2,--.

Signed and Sealed this

Ninth Day of July 1985

[SEAL]

Attest:

DONALD J. QUIGG

Attesting Officer          Acting Commissioner of Patents and Trademarks